United States Patent [19]

Morey et al.

[11] 4,383,221
[45] May 10, 1983

[54] WATER RESISTIVITY SENSOR

[75] Inventors: Kenneth H. Morey, Framingham; Steven C. Dark, Groton, both of Mass.

[73] Assignee: Millipore Corporation, Bedford, Mass.

[21] Appl. No.: 199,277

[22] Filed: Oct. 21, 1980

[51] Int. Cl.³ .............................................. G01N 27/02
[52] U.S. Cl. .................................... 324/439; 324/442; 324/441; 324/446
[58] Field of Search ............... 324/439, 441, 442, 446, 324/450

[56] References Cited

U.S. PATENT DOCUMENTS

| | | | |
|---|---|---|---|
| 3,000,805 | 9/1961 | Carritt | 324/441 |
| 3,334,745 | 3/1966 | Burgess et al. | |
| 3,710,237 | 1/1973 | Watson | 324/446 |
| 3,919,627 | 11/1975 | Allen | 324/442 |
| 4,035,719 | 7/1977 | Anderson | 324/443 |
| 4,082,666 | 4/1978 | Jones et al. | |

OTHER PUBLICATIONS

Series MG-MHO GUN; "A New and Better Idea in Portable Conductivity Measurement"; Beckman.
"Conductivity Ratio Solu Meter Series SM-RA"; Beckman.
Product Specification PSS 6-3A1A Series 910M, 915M, 915N, and 915H Balsbaugh Conductivity Monitors; Foxboro.

Primary Examiner—Michael J. Tokar
Attorney, Agent, or Firm—David Prashker; Paul J. Cook

[57] ABSTRACT

A compact, battery-powered water resistivity sensor measures the resistivity of water, sequentially compares the measured resistivity to a plurality of predetermined resistivities, and numerically displays that one of the plurality of predetermined resistivities approximating the measured resistivity. Preferably, the pair of electrodes consists of a pair of printed circuit electrodes disposed conveniently on the end face of an insulating nut extending, in fluid-tight fashion, into the tank of water. The sensor is powered by a battery, and includes circuitry for interrupting the supply of battery power to various circuit elements, the functions of which elements are no longer needed once the water resistivity is determined by the sensor. The sensor also includes temperature-sensitive compensation means responsive to changes in the water temperature for varying an input signal provided to the electrodes. Finally, the sensor includes a low battery condition detection means responsive to the low battery condition for displaying a corresponding low battery indicator.

21 Claims, 11 Drawing Figures

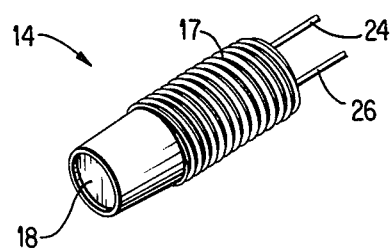
FIG. 2A
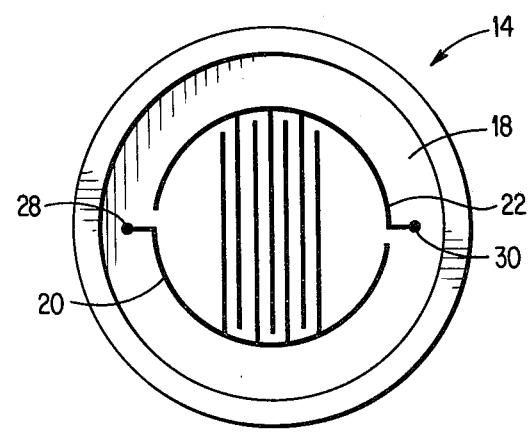
FIG. 2B
FIG. 3B
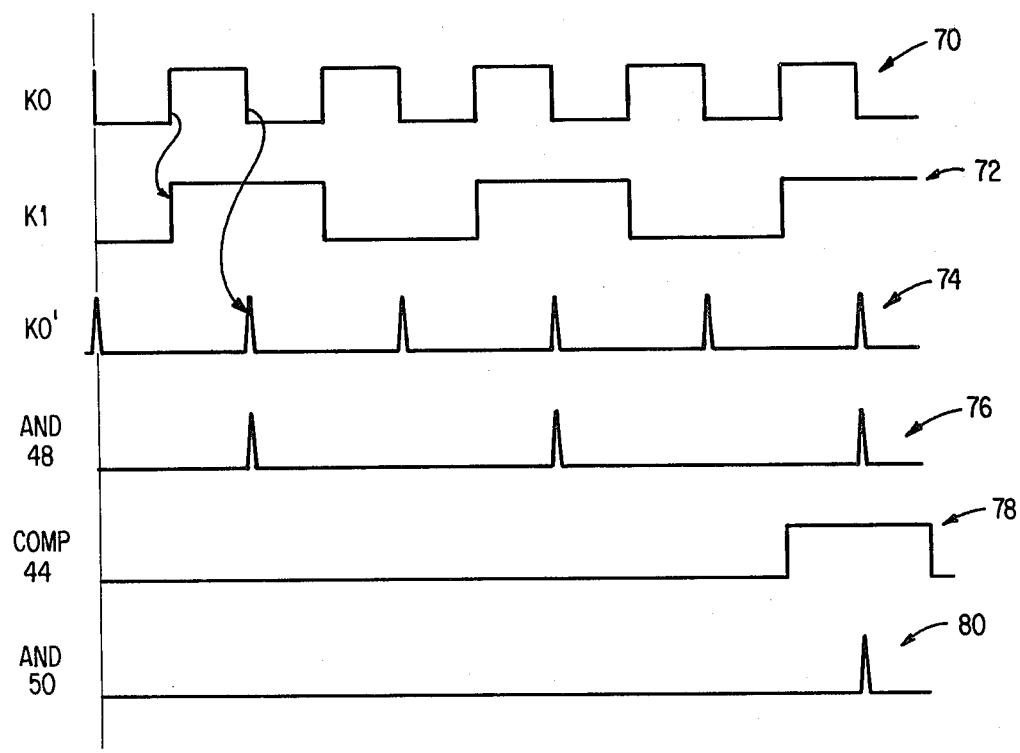

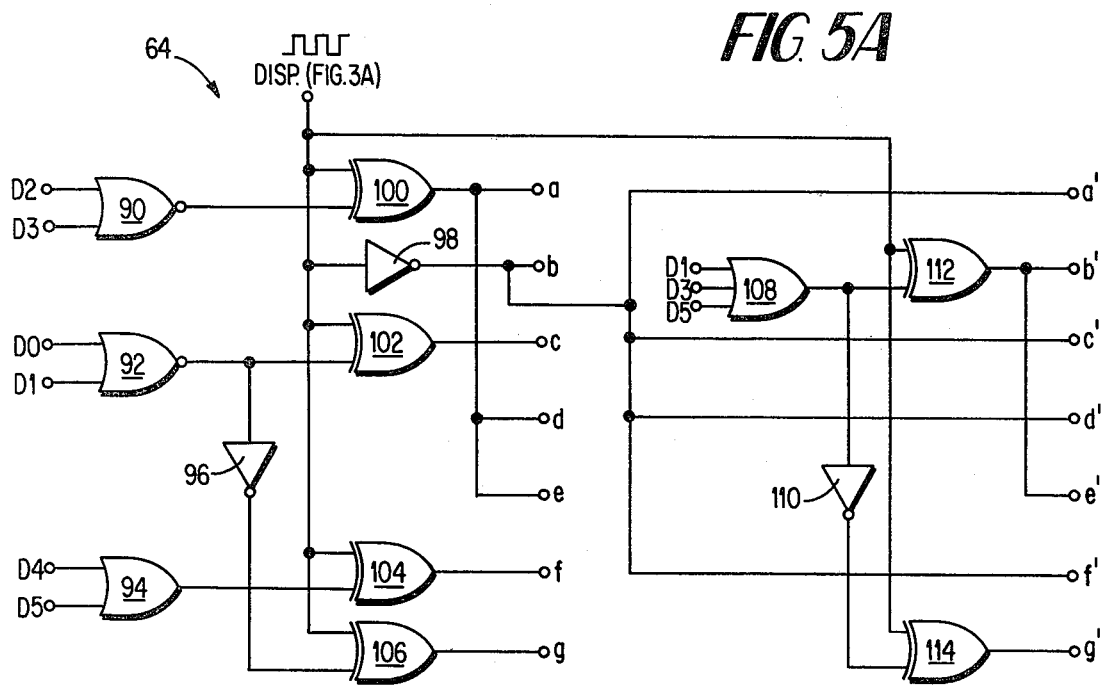
FIG. 5A
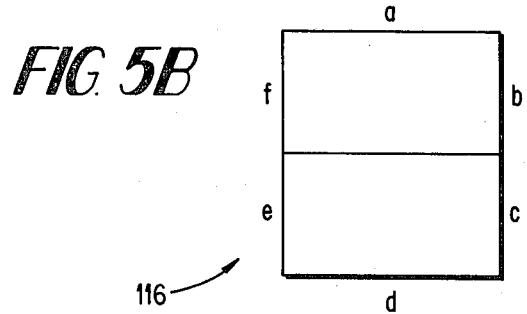
FIG. 5B
FIG. 5C
| COUNTER | DISPLAY | FIRST DIGIT | | | | | | | SECOND DIGIT | | | | | | |
|---|---|---|---|---|---|---|---|---|---|---|---|---|---|---|---|
| | 118 | a | b | c | d | e | f | g | a' | b' | c' | d' | e' | f' | g' |
| D0 | 2.5 | 1 | 1 | 0 | 1 | 1 | 0 | 1 | 1 | 0 | 1 | 1 | 0 | 1 | 1 |
| D1 | 2.0 | 1 | 1 | 0 | 1 | 1 | 0 | 1 | 1 | 1 | 1 | 1 | 1 | 1 | 0 |
| D2 | 1.5 | 0 | 1 | 1 | 0 | 0 | 0 | 0 | 1 | 0 | 1 | 1 | 0 | 1 | 1 |
| D3 | 1.0 | 0 | 1 | 1 | 0 | 0 | 0 | 0 | 1 | 1 | 1 | 1 | 1 | 1 | 0 |
| D4 | 0.5 | 1 | 1 | 1 | 1 | 1 | 1 | 0 | 1 | 0 | 1 | 1 | 0 | 1 | 1 |
| D5 | 0.0 | 1 | 1 | 1 | 1 | 1 | 1 | 0 | 1 | 1 | 1 | 1 | 1 | 1 | 0 |

WATER RESISTIVITY SENSOR

BACKGROUND OF THE INVENTION

1. Field of the Invention

The present invention relates to a water resistivity sensor, and more particularly to a compact, battery-powered water resistivity sensor, by means of which resistivity of water can be measured and displayed in terms of actual resistivity values.

2. Description of the Prior Art

Prior art arrangements for sensing water resistivity have been encumbered by several disadvantages. Notable among these disadvantages are: (1) inability to keep power applied to the sensor to a minimum, thus making it difficult to meet safety requirements; (2) inability to minimize power consumed by the sensor; (3) failure to measure and display actual resistivity values; (4) difficulty in developing a compact water resistivity sensor; and (5) failure to develop an inexpensive sensor unit.

For example, in certain arrangements, a signaling light is energized to indicate the end point of useful life of water contained in a storage tank. In such an arrangement, a predetermined conductivity of the water is set, and a lamp is kept energized so long as the conductivity of the water remains below a predetermined point. Power wires are provided for bringing standard household current (115 volt A.C.) to the indicator bulb and the probes, the latter being encapsulated in a common housing. Thus, such an arrangement is characterized by most, if not all, of the disadvantages enumerated above.

In another arrangement of the prior art, an end point quality control light circuit is powered by standard household current, and includes a pair of probes isolated from the source of power. However, the subject circuit applies only 12 volts (approximately) to the water being monitored. Nevertheless, the quality of the water is only indicated by an indicator lamp. Thus, whereas this arrangement does attempt to overcome the first disadvantage enumerated above, the other disadvantages still remain.

SUMMARY OF THE INVENTION

As stated above, the present invention relates to a water resistivity sensor, and more particularly to a compact, battery-powered water resistivity sensor which overcomes each of the disadvantages enumerated above.

Basically, the water resistivity sensor of the present invention comprises inexpensive and easily reproducible printed electrodes which are immersed in the water, simplified circuitry for determining the resistivity of the water to within a predetermined megohm/cm. interval, and a display unit for displaying the resistivity value measured. Prior art practitioners have typically employed electrodes comprising parallel-pin or rod sensors, the latter being expensive and difficult to fabricate, and not being easily capable of reproduction. Accordingly, in accordance with one feature of the present invention, printed circuit electrodes are employed, such printed circuit electrodes being inexpensive and easily reproducible.

The simplified circuitry of the present invention basically comprises generator circuitry for applying current to one of the electrodes, sensing circuitry connected to the other electrode for determining the resistivity (or inversely, the conductivity) of the water, reference circuitry for sequentially providing decreasing reference values of resistivity (or increasing values of conductivity), a comparator for comparing the sensed resistivity of the water with the sequentially received decreasing reference values of resistivity, further circuitry for halting the operation of the unit once a reference resistivity value approximating the resistivity of the water is found, and a display circuit for displaying the particular reference value of resistivity approximating the actual measured water resistivity. As will become more clear below, the operation and design of the sensor of the present invention is such that circuitry is very much simplified, and thus the water resistivity sensor is able to be housed within a compact unit.

In addition, as a result of the sophisticated design of the water resistivity sensor circuitry, the sensor is capable of being battery-powdered, thus facilitating avoidance of safety hazards normally encountered when line voltage (115 volt A.C.) is utilized, while at the same time minimizing power consumption of the unit. In fact, in accordance with a further feature of the present invention, circuitry is provided for halting the application of power to certain portions of the resistivity measuring circuitry, thus reducing overall power consumption, extending the life of various circuit elements (such as amplifiers), and achieving extended life of the batteries powering the water resistivity sensor.

As will be seen below, the display unit of the water resistivity sensor preferably comprises a seven-segment liquid crystal display (LCD). As will also be seen below, further simplification of the circuitry of the present invention is achieved by specially designing the display driver circuitry so as to develop only those display driver signals necessary for display of the particular resistivity values occurring within a given range of resistivity at given intervals (for example, occurring within the range of 0-3 megohm/cm. at intervals of 0.5 megohm/cm.).

As will be discussed in more detail below, the inventive water resistivity sensor of the present application provides compensation for change in water temperature. More specifically, the amplitude of the input signal provided to one of the electrodes of the sensor is varied, by means of a voltage-divider network which includes a thermistor, so as to compensate for water temperature changes.

In addition, the water resistivity sensor is provided with circuitry for detecting a low battery condition, and a low battery indication is displayed on the display device of the unit.

Therefore, it is an object of the present invention to provide a water resistivity sensor, and more particularly to provide a compact, battery-powdered water resistivity sensor.

It is an additional object of the present invention to provide a water resistivity sensor which, by virtue of being battery-powered, easily avoids safety hazards normally associated with the utilization of line voltage, thus easily meeting contemporary electrical safety standards.

It is an additional object of the present invention to provide a water resistivity sensor which has minimal power consumption.

It is an additional object of the present invention to provide a water resistivity sensor which displays actual resistivity values closely approximating, if not coinciding with, the resistivity of the water being measured.

It is an additional object of the present invention to provide a water resistivity sensor having a simplified circuit design so as to facilitate housing of the water resistivity sensor within a compact unit.

It is an additional object of the present invention to provide a water resistivity sensor which employs printed circuit electrodes which are inexpensive to produce and capable of easy reproduction.

It is an additional object of the present invention to provide a water resistivity sensor having circuitry for halting application of power to various circuit elements when such circuit elements are not in use, thus providing a further means for minimizing power consumption.

It is a further object of the present invention to provide a water resistivity sensor including circuitry for providing automatic compensation for changes in water temperature.

It is a further object of the present invention to provide a water resistivity sensor having circuitry for detecting a low battery condition, such low battery condition being displayed on the display device of the sensor unit.

The above and other objects that will hereinafter appear, and the nature of the invention, will be more clearly understood by reference to the following description, the appended claims, and the accompanying drawings.

BRIEF DESCRIPTION OF THE DRAWINGS

FIG. 2A is a side view of an insulating nut which is screwed in a fluid-tight manner into an opening in the wall of the water storage tank, and which carries the printed circuit electrodes of the water resistivity sensor.

FIG. 2B is an end view of the insulating nut, depicting the printed circuit electrodes positioned on the end face of the insulating nut.

FIG. 3B is a timing diagram relating to the operation of the circuit of FIG. 3A.

FIG. 5A is a logic diagram of the display driver of FIG. 3A.

FIG. 5B is a diagrammatic representation of one digit position of the liquid crystal display device employed in the display unit of the present invention.

FIG. 5C includes a series of tables depicting the segment-driving signals for the 2-digit positions of the display device of the water resistivity sensor.

DETAILED DESCRIPTION

The present invention will now be more fully described with reference to the various figures of the drawings.

Figure 1A:
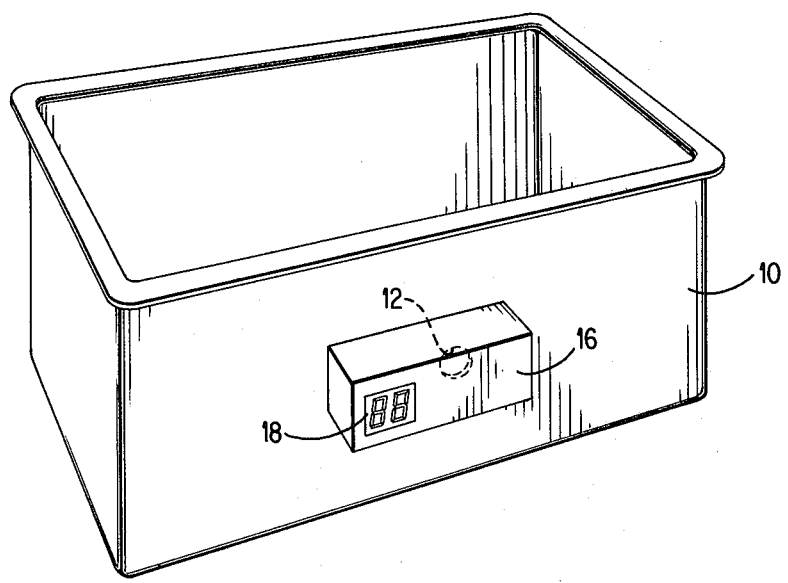
FIGS. 1A and 1B are a perspective view and a top view, respectively, of the water resistivity sensor of the present invention employed in association with a water storage tank.
Figure 1B:
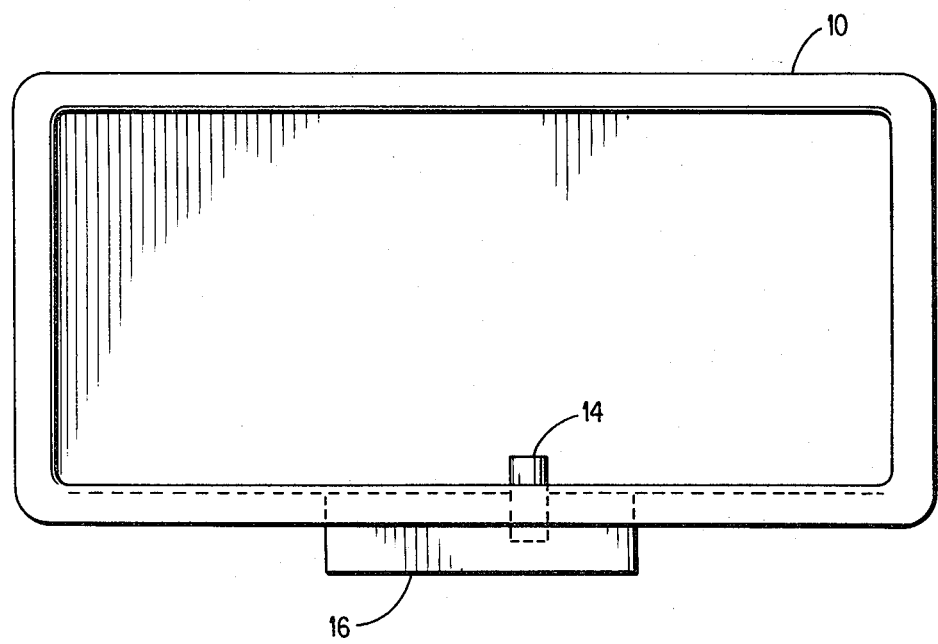

As stated above, FIGS. 1A and 1B are a perspective view and a top view, respectively, of the water resistivity sensor employed with a water storage tank.

More specifically, as seen in FIGS. 1A and 1B, a water storage tank 10 is provided with a hole 12 in its wall, and an insulating nut 14 is screwed in a fluid-tight manner through the hole 12 in the wall of the storage tank 10. The water resistivity sensor unit 16 is then secured to the outer surface of the wall of the storage tank 10 so as to cover the insulating nut 14 as it protrudes from the outer surface of the wall of the storage tank 10. The water resistivity sensor 16 includes (as will be discussed in more detail below) a circuit board and battery enclosed within a cover having a viewing window, the latter exposing a display device 18 (such as a liquid crystal display device).

FIG. 2A is a side view of the insulating nut 14. As seen in FIG. 2A, the insulating nut 14 has a threaded portion 17 which facilitates fluid-tight screwing of the insulating nut 14 into the opening 12 in the wall of the storage tank 10, as described above. It is to be understood that a hex nut (not shown) or other means for securing the insulating nut 14 in the wall of the storage tank 10 in a fluid-tight manner may be employed.

The insulating nut 14 has an end face 18, which is best seen in FIG. 2B. The printed circuit electrodes 20 and 22 are disposed on the end face 18 (preferably, in a recess formed therein) of the insulating nut 14 so that, when the insulating nut 14 is screwed in a fluid-tight manner through the opening 12 in the wall of the storage tank 10, the electrodes 20 and 22 contact the water within the tank 10. Further referring to FIGS. 2A and 2B, electrode leads 24 and 26 are connected via connections 28 and 30 to the electrodes 20 and 22, respectively, and the electrode leads 24 and 26 extend through the interior of the insulating nut 14 so as to protrude therefrom, thus facilitating connection to the printed circuit board (not shown) within the water resistivity sensor 16.

The printed electrodes 20 and 22 can take any suitable form so as to array the electrodes in spaced relationship and in contact with the water. For example, electrodes 20 and 22 may take the form of concentric conductors, with alternate conductors being connected in parallel to one or the other of the electrode leads 24 and 26. Similarly, the electrodes 20 and 22 may take the form of spaced spirals. However, it has been found that the aforementioned two arrangements are quite complicated in terms of fabrication, and necessitate the utilization of external electrode connections. Accordingly, a preferred embodiment of the present invention provides electrodes 20 and 22, as shown, in the form of opposing semi-circular elements, each having projecting linear conductors disposed in a spaced relationship, thus providing for much easier electrical connection of the electrodes 20 and 22.

Finally, the printed electrodes 20 and 22 may be formed in any conventional manner. For example, the electrode patterns may be formed in copper on a glass epoxy, and may then be covered with a nickel and gold plating. The resulting printed circuit is then fixed to a recess in the end face 18 of the insulating nut 14, and electrode leads 24 and 26 are (as previously described) connected to the electrodes 20 and 22 at points 28 and 30, respectively. Then, as a final step, the interior of the insulating nut 14 is preferably filled with epoxy so as to render the resulting device structurally stable.

Figure 3A:
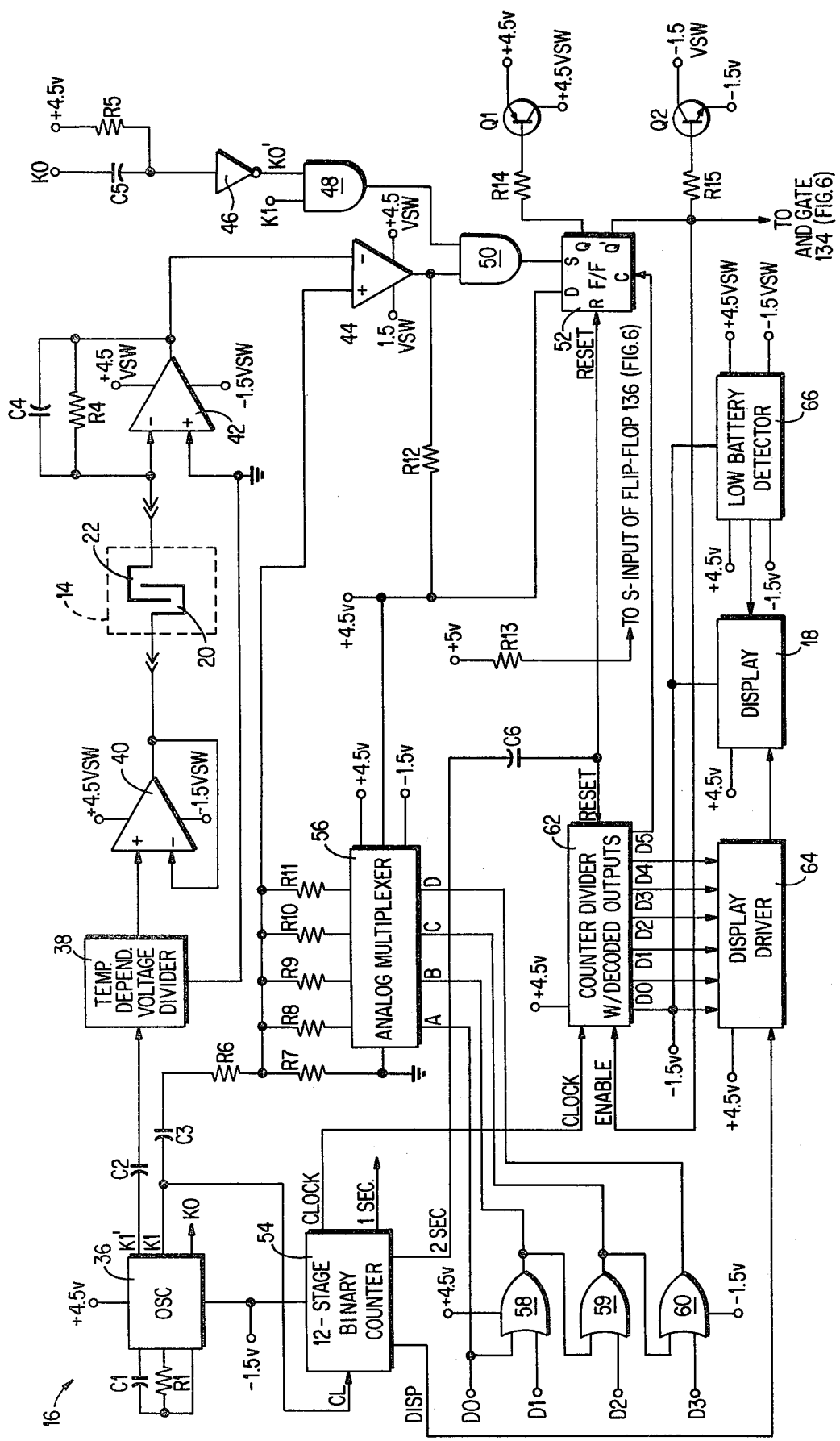
FIG. 3A is a diagrammatic representation of the water resistivity sensor of the present application.

FIG. 3A is a diagrammatic representation of the water resistivity sensor of the present invention. As seen therein, water resistivity sensor 16 comprises the following elements: an oscillator 36, a temperature-dependent voltage divider 38, op amp 40 connected to one of the electrodes 20, op amp 42 having one input connected to the other electrode 22, voltage comparator 44, inverter 46 and AND gate 48, AND gate 50, flip-flop 52, twelve-stage binary counter 54, analog multiplexer 56, OR gates 58–60, counter divider (with decoded outputs) 62, and display driver 64 and low battery detector 66 connected to the display 18.

Operation of the water resistivity sensor 16 of FIG. 3 is as follows. Oscillator 36 operates, in accordance with the RC circuit formed by resistor R1 and capacitor C1, to generate a basic clock signal K0 and a further clock signal K1 representing signal K0 frequency-divided by 2. In addition, oscillator 36 generates inversely related clock signal K1'. In the preferred embodiment, oscillator 36 is a CD4047 device (manufactured by RCA).

The output K1' is AC-coupled (to remove D.C. components), via capacitor C2, to a temperature-dependent voltage divider 38, while the output K1 of oscillator 36 is provided directly to the twelve-stage binary counter 54 as a clock input CL thereto, while at the same time being AC-coupled, via capacitor C3, and provided, via the voltage divider formed by resistor R6 in combination with further resistors R7–R11, to the positive input of voltage comparator 44.

The K1' output of oscillator 36 is, preferably, a 1 kHz square wave, and is provided via capacitor C2 to the temperature-dependent voltage divider 38. The temperature-dependent voltage divider 38 adjusts the amplitude of the 1 kHz square wave to provide compensation for changes in water temperature. The operation of the temperature-dependent voltage divider 38 will be discussed in more detail below, with reference to FIG. 4.

The adjusted square wave output of temperature-dependent voltage divider 38 is buffered to a very low impedance by an operational amplifier 40, connected in a voltage-follower configuration. This provides the electrode 20 (located within the sensor insulating nut 14) with a low-impedance source input.

The electrode 22 is connected to the inverting input of further op amp 42, the non-inverting input of which is grounded. The output of op amp 42 is a square wave having an amplitude directly proportional to the conductivity, and thus inversely proportional to the resistivity, of the water in the storage tank 10 (FIG. 1A). Moreover, the output of op amp 42 is provided to the inverting input of voltage comparator 44, the non-inverting input of which is connected to the voltage-dividing network formed by resistor R6 in combination with resistors R7–R11. However, it is to be noted that resistors R8–R11 are connected to an analog multiplexer 56, the operation of which will be described below.

The twelve-stage binary counter 54 is, as previously mentioned, clocked by the K1 output of oscillator 36. The counter 54 issues an output CLOCK for clocking counter divider (with decoded outputs) 62, and it also (by conventional frequency-division techniques) provides output 1SEC occurring at one second intervals, output 2SEC occurring at two second intervals, and output DISP having an appropriate frequency for clocking the display driver 64. The output 2SEC of counter 54 is utilized to reset, via capacitor C6, the flip-flop 52 and counter divider 62. Upon being reset, flip-flop 52 raises its K1' output to a high level, so as to enable the counter divider 62.

Counter divider 62, in accordance with the CLOCK input from counter 54, sequentially issues signals D0–D5 which (as will be seen below) define various time intervals in the operation of the water resistivity sensor 16. Outputs D0–D5 of counter divider 62 are provided to display driver 64, while outputs D0–D3 are provided an inputs to OR gates 58–60.

OR gates 58–60 form the control logic for operation of the analog multiplexer 56. Specifically, analog multiplexer 56 (which is preferably a CD4066 device, manufactured by RCA) responds to the inputs A–D (corresponding to output D0 of counter divider 62 and the respective three outputs or OR gates 58–60) to perform the following operations: (1) during a first time interval defined by output D0, multiplexer 56 connects each of resistors R8–R11 to ground; (2) during a second time interval defined by output D1, multiplexer 56 disconnects resistor R8 from ground, leaving resistors R9–R11 connected to ground; (3) during a third time interval defined by output D2, multiplexer 56 disconnects resistor R9 from ground, leaving resistors R10 and R11 connected to ground; (4) during a fourth time interval defined by output D3, multiplexer 56 disconnects resistor R10 from ground, leaving resistor R11 connected to ground; and (5) during a fifth time interval indicated by outputs D0–D3 being inactive, multiplexer 56 disconnects resistor R11 from ground, leaving no resistors connected to ground (except for resistor R7 which is externally connected to the multiplexer 56). As a result of this operation, multiplexer 56 provides successively increasing voltage inputs to the non-inverting input of voltage comparator 44.

Thus, voltage comparator 44 performs sequential comparisons of the conductivity-related output of op amp 42 to successively increasing conductivity reference values, or, stated in other words, comparator 44 performs sequential comparisons of the resistivity indicated by the amplitude of the output of op amp 42 to successively decreasing resistivity reference values. When a resistivity reference value less than the resistivity indicated by op amp 42 is first detected, voltage comparator 44 issues an output which, via AND gate 50 (when enabled), sets the flip-flop 52.

FIG. 3B is a timing diagram relating to the operation of op amp 42, voltage comparator 44 and AND gate 50, in conjunction with inverter 46 and AND gate 48. Specifically, the output K0 of oscillator 36 is shown as waveform 70 in FIG. 3B, and is provided to a differentiation circuit comprising capacitor C5 in parallel with resistor R5. The resulting differentiated signal, once inverted by inverter 46, appears as signal K0', indicated by waveform 74. The latter is gated with signal K1 in AND gate 48, output K1 (waveform 72) being a frequency-divided version of output K0. The resulting output of AND gate 48 is shown as waveform 76, and is provided to AND gate 50, the other input of which receives the output of voltage comparator 44. It will be recalled that, once the resistivity reference input (non-inverting input) to voltage comparator 44 is less than the resistivity-related output of op amp 42, voltage comparator 44 issues a high output (the square wave in waveform 78). Once this positive input is provided to AND gate 50, the pulse output of AND gate 48 is permitted to pass through to the set input of flip-flop 52, thus setting the flip-flop 52.

Continuing with the discussion of the operation of the water resistivity sensor 16 of FIG. 3A, so long as the flip-flop 52 remains in the reset state, counter divider 62 is enabled, and continues to sequentially issue outputs D0–D5 to the display driver 64, as well as outputs D0–D3 to the analog multiplexer 56 and associated OR gates 58–60. In addition, in the reset state, flip-flop 52 issues a low Q output via resistor R14 to the base of PNP transistor Q1, causing it to conduct, and a high Q' output via resistor R15 to the base of NPN transistor Q2, causing it to conduct. In this manner, transistors Q1 and Q2 function as power-controlling transistors to maintain application of power (preferably, +4.5 volts and −1.5 volts) to various circuit elements of the sensor 16, for example, the op amps 40 and 42, comparator 44, and low battery detector 66. However, once the AND gate 50 sets the flip-flop 52, the Q output of flip-flop 52 goes high and the Q' output goes low, causing transistors Q1 and Q2 to turn off. This results in removal of power from the aforementioned elements of the sensor 16. Thus, a unique feature of the present invention resides in the fact that, once the sensor 16 obtains the water resistivity value, the flip-flop 52 is set so as to remove power from the various aforementioned elements of the circuit 16. Significant savings in power are a result.

It is to be further noted that, once the sensor 16 determines the water resistivity value, resetting of flip-flop 52 disables the counter divider 62, thus freezing the output (one of the outputs D0–D4) of counter divider 62. The particular frozen output of counter divider 62, thus, indicates the particular time interval during which the voltage comparator 44 obtained a positive comparison result, and thus further indicates the particular resistivity-related reference voltage input to comparator 44 which resulted in the positive comparison output. Therefore, the particular frozen output of counter divider 62 corresponds to that resistivity value (from among five predetermined resistivity values) just less than the actual resistivity of the water. As will be seen below, this information is decoded by decoding circuitry contained in the display driver 64, and the particular resistivity value is accordingly displayed in display 18.

Considering the example previously mentioned, wherein resistivity values range from 0 to 2.5 megohm/cm. in intervals of 0.5 megohm/cm., if counter divider 62 is disabled during output D0, the resistivity value of 2.5 megohm/cm. would be displayed in display 18. Similarly, if output D1 is active during the disabling of counter divider 62, a resistivity of 2.0 megohm/cm. is indicated.

As previously stated, the circuitry of sensor 16 has an automatic restart capability, in that twelve-stage binary counter 54 issues an output 2SEC every two seconds, and this output is utilized to reset counter divider 62 and flip-flop 52, the Q' output of flip-flop 52 acting as an input ENABLE to the counter divider 62.

Figure 4:
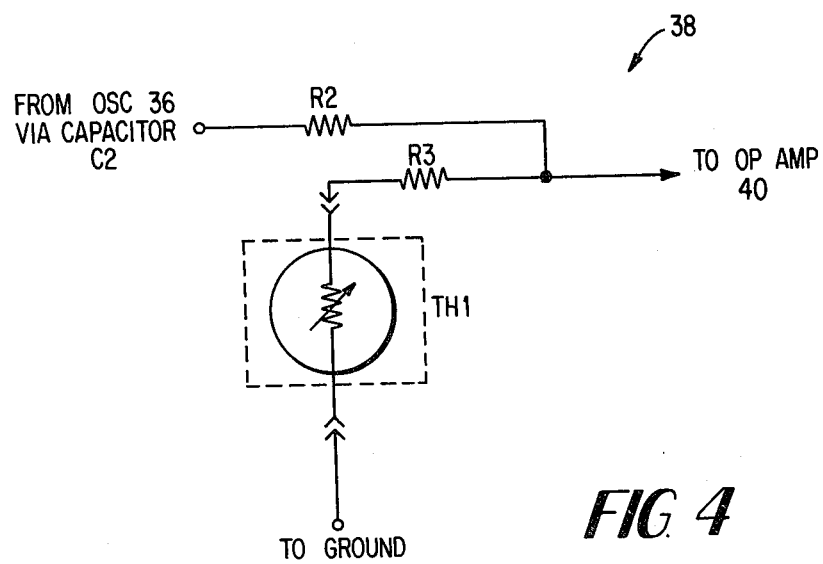
FIG. 4 is a circuit diagram of the temperature-dependent voltage divider of FIG. 3A.

FIG. 4 is a circuit diagram of the temperature-dependent voltage divider 38 of FIG. 3A. As seen therein, the temperature-dependent voltage divider 38 comprises resistors R2 and R3, in combination with thermistor TH1. In a preferred embodiment of the present invention, thermistor TH1 is placed in or near the water so as to detect water temperature. The thermistor TH1 varies in resistance in accordance with the detected temperature of the water, so as to vary the total branch resistance (that is, its own resistance plus the resistance of resistor R3). Since resistor R2 is connected in a voltage-division arrangement with resistor R3 and thermistor TH1, variation of the resistance of thermistor TH1 results in an adjustment in the amplitude of the signal from oscillator 36 via capacitor C2, the amplitude-adjusted output being provided to op amp 40. Compensation for change in water temperature is thus achieved.

FIG. 5A is a logic diagram of the display driver 64; FIG. 5B is a seven-segment display indicator as preferably employed in the display 18 of FIG. 3A; and FIG. 5C depicts the output conditions/segment-driving signals corresponding to the various frozen outputs of the counter divider 62 of FIG. 3A.

As seen in FIG. 5A, the display driver 64 comprises NOR gates 90 and 92, OR gate 94, inverters 96 and 98, and exclusive-OR gates 100, 102, 104 and 106, the latter arrangement being clocked by output DISP of counter 54 (FIG. 3A), and being responsive to the various possible outputs D0–D5 of counter divider 62 (FIG. 3A) for deriving segment-driving signals a–g and a', c', d' and f'. As further seen in FIG. 5A, the display driver 64 also includes OR gate 108, inverter 110 and exclusive-OR gates 112 and 114, the latter being clocked by signal DISP, and responding to any one of the outputs D1, D3 or D5 of counter divider 62 for providing the segment-driving signals b', e' and g'.

Referring to FIGS. 3A and 5B, the display 18 is preferably made up of a two-position display, each position comprising a conventional seven-segment display indicator 116 (as seen in FIG. 5B). Accordingly, display driver 64 provides first position segment-driving signals a–g to designate the first numeral of the sensed water resistivity, and further provides segment-driving signals a'–g' to the second position so as to display the second numeral of the detected water resistivity.

FIG. 5C shows (in table 118) the various outputs of counter divider 62 in correspondence to the respective water resistivity values detected and displayed. In addition, tables 120 and 122 show the various segment-driving signals a–g and a'–g', respectively, provided to the first and second digit positions in the display 18.

Referring to FIGS. 5A–5C, it is to be noted that, in accordance with a feature of the present invention, substantially simplified design of the display driver circuit 64 is achieved by taking advantage of the fact that the measured resistivity of the water can only take on one of a predetermined number (in the present embodiment, six) of values. This simplified circuit design, together with other features of the present invention, facilitates packaging of the water resistivity sensor into a compact sensor unit.

Figure 6:
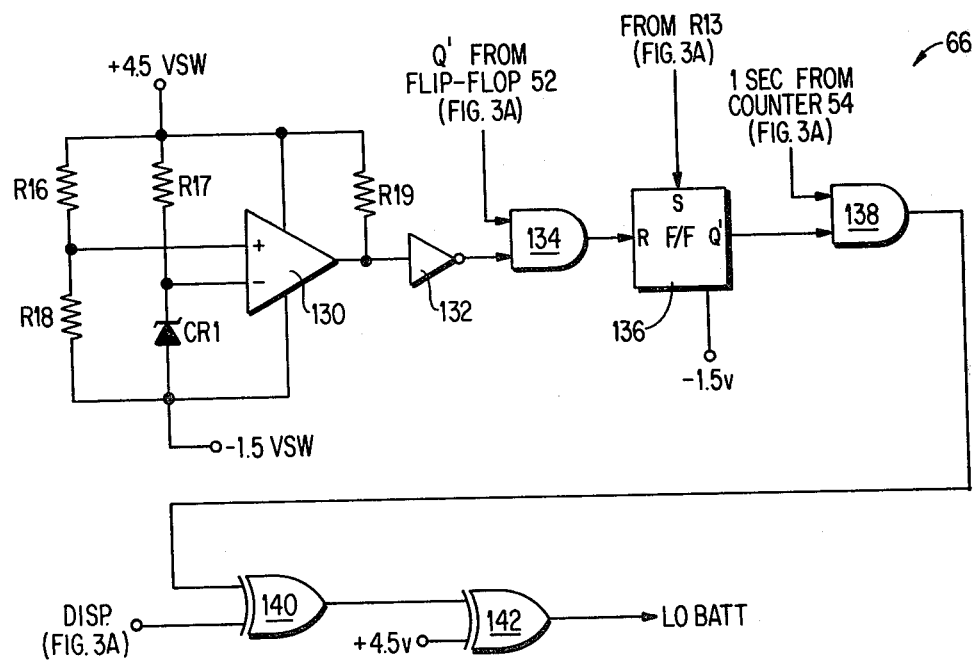
FIG. 6 is a detailed diagram of the low battery detector of FIG. 3A.

FIG. 6 is a circuit diagram of the low battery detector 66 of FIG. 3A. As seen therein, the low battery detector 66 basically comprises zener diode CR1 and associated resistors R16–R18, voltage comparator 130 and associated resistor R19, inverter 132, AND gate 134, flip-flop 136, AND gate 138 and exclusive-OR gates 140 and 142.

In operation, voltage comparator 130 detects a divided-down voltage from the battery, such being detected via resistors R16 and R18. In addition, a reference voltage, derived from zener diode CR1, is presented to the inverting input of voltage comparator 130. So long as a low battery condition does not exist, voltage comparator 130 issues a high output which, after inversion by inverter 132, appears as a low input to AND gate 134. Thus, flip-flop 136 remains in its set state, causing a low Q' output from flip-flop 136 to maintain AND gate 138 not enabled. As a result, gate 138 provides a low output to exclusive-OR gate 140 which, in turn, causes the display driving signal DISP (from counter 54 of FIG. 3A) to be passed through exclusive-OR gate 140 and inverted by inverting exclusive-OR gate 142. As a result, a low battery indication is not displayed on the display device 18. More specifically, in the preferred embodiment, during non-occurrence of low battery condition, a decimal point between the two digit positions remains continuously displayed.

Conversely, when a low battery condition exists, such is detected by voltage comparator 130 which issues a low output, the latter being inverted by inverter 132 and provided as a high input to AND gate 134. This high input passes through gate 134, when the latter is enabled by the Q' output of flip-flop 52 (FIG. 3A), causing the flip-flop 136 to be reset. Flip-flop 136 then issues a high Q' output to AND gate 138, causing the 1SEC input from the counter 54 (FIG. 3A) to be provided to the exclusive-OR gate 140. It is to be recalled that the signal 1SEC is an alternating square wave of given frequency (1 Hz.). Accordingly, exclusive-OR gate 140 operates at a frequency corresponding to the 1SEC input thereto so as to alternately normal through and invert the display driving signal DISP, the latter being further inverted by inverting exclusive-OR gate 142, and provided to the display device 18. The result is that, during low battery condition, the decimal point appearing between the two digit positions in the display device 18 blinks on and off at a frequency corresponding to signal 1SEC, thus alerting the operator to a low battery condition.

While preferred forms and arrangements have been shown in illustrating the invention, it is to be clearly understood that various changes in detail and arrangement may be made without departing from the spirit and scope of this disclosure.

What is claimed is:

1. A water resistivity sensor for indicating the resistivity of water comprising:
   electrode means for generating a signal proportional to the resistivity of the water;
   circuit means for processing said signal from said electrode means and issuing an output signal corresponding to the resistivity of the water, wherein said electrode means comprises a reference circuit sequentially providing successive voltage values corresponding to successive, resistivity values, and a voltage comparator connected to said electrode means and to said reference circuit for comparing said signal from said electrode means to each successive voltage value so as to determine that one of said successive voltage values approximates said signal from said electrode means, whereby the resistivity of the water is determined; and
   display means responsive to said output signal of said circuit means for displaying the resistivity of the water.

2. A sensor unit for measuring the resistivity of water contained in a tank comprising:
   a pair of electrodes generating a signal proportional to the resistivity of the water;
   electrode carrying means for carrying said pair of electrodes through said tank so as to cause said electrodes to contact the water;
   circuit means in communication with said pair of electrodes, said circuit means comprising a reference circuit sequentially providing successive voltage values corresponding to successive resistivity values, and a voltage comparator connected to said pair of electrodes and to said reference circuit for comparing said signal from said pair of electrodes to each said successive voltage values so as to determine that one of said successive voltage values approximates said signal from said pair of electrodes, whereby the resistivity of the water is determined; and
   display means connected to said circuit means for displaying the resistivity of the water.

3. A water resistivity sensor for indicating the resistivity of water comprising:
   generator means for generating a signal;
   printed circuit electrode means connected to said generator means and being positioned in said water for receiving said signal and providing an output signal proportional to the resistivity of said water;
   circuit means for processing said output signal of said printed circuit electrode means and issuing an output signal corresponding to the resistivity of said water, wherein said circuit means comprises a reference circuit sequentially providing successive voltage values corresponding to respective successive resistivity values, and a voltage comparator connected to said electrode means and to said reference circuit for comparing said output signal of said electrode means to each said respective successive voltage value so as to determine that one of said successive voltage values approximates said output signal of said electrode means, whereby to determine said resistivity of said water; and
   display means responsive to said output signal of said circuit means for numerically displaying said resistivity of said water.

4. The sensor of claim 3, wherein said circuit means comprises a counter responsive to provision of said successive voltage values by said reference circuit for counting through respective successive count states to develop corresponding successive count outputs, said display means comprising a decoder responsive to that one of said successive count outputs corresponding to said one of said successive voltage values determined by said comparator for deriving a minimum number of display driving signals for displaying that one of said respective successive resistivity values corresponding to said one of said successive voltage values approximating said output signal of said electrode means.

5. The sensor of claim 3, said generator means comprising temperature-sensitive compensation means responsive to the temperature of said water for adjusting said signal provided by said generator means to said electrode means in accordance therewith, whereby to compensate the water temperature changes.

6. The sensor of claim 3, further comprising a battery, and low battery detector means connected to said battery for detecting a low battery condition, said display means being connected to said low battery detector means and responsive to detection of said low battery condition for displaying a low battery indication signal.

7. The sensor of claim 3, further comprising battery means for supplying power to said generator means, said electrode means, said circuit means and said display means, and interruption means for interrupting said power provided by said battery means once said resistivity of said water is determined by said circuit means.

8. The sensor of claim 1, wherein said circuit means comprises a counter responsive to said provision of said successive voltage values of said reference circuit for counting through a corresponding number of count states to develop successive respective count outputs, said display means comprising a display drive circuit responsive to that one of said successive count outputs corresponding to said one of said successive voltage values determined by said comparator for issuing a minimum number of drive signals for displaying that one of said respective successive resistivity values corresponding to that one of said successive voltage values approximating said signal from said electrode means.

9. The sensor of claim 1, further comprising temperature-sensitive compensation means connected between said circuit means and said electrode means, and responsive to a change in the temperature of said water for adjusting said input signal provided by said circuit means to said electrode means, whereby to compensate for said change in the temperature of said water.

10. The sensor of claim 1, further comprising a battery, and low battery detection means connected to said battery for determining a low battery condition thereof, said display means being connected to said low battery detection means for displaying a low battery indication.

11. The sensor of claim 1, further comprising battery means for supplying power to said circuit means, and interruption means for interrupting said power supplied by said battery means once said resistivity of said water is determined by said circuit means.

12. The unit of claim 2, wherein said pair of electrodes comprises a pair of printed circuit electrodes arranged in spatical relationship with respect to each other.

13. The unit of claim 2, wherein said electrode carrying means comprises a threaded insulating nut extending through said tank to the interior thereof, said threaded insulating nut having an end face extending into the interior of said tank and carrying said pair of electrodes.

14. The unit of claim 12, wherein said circuit means comprises a printed circuit board.

15. The unit of claim 12, wherein said circuit means provides an input signal to one of said pair of electrodes, said unit further comprising temperature-sensitive compensation means responsive to change in the temperature of said water for adjustably varying said input signal provided by said circuit means to said pair of electrodes.

16. The unit of claim 12, wherein said sensor unit is powered by a battery, said unit including low battery detection means connected to said battery for detecting a low battery condition of said battery, said display means being connected to said low battery detection means for displaying a low battery indicator.

17. The unit of claim 12, wherein said electrode carrying means comprises an insulating nut having an end face which is recessed, said pair of electrodes comprising printed circuit electrodes positioned in said recessed end face of said insulating nut.

18. The unit of claim 12, comprising battery means for powering said circuit means and said display means, and interruption means connected to said battery and to said circuit means for interrupting said power supply to said circuit means and said display means when said circuit means determines said resistivity of said water.

19. The unit of claim 2, said circuit means comprising a counter responsive to said provision of said successive voltage values by said reference circuit for counting through a plurality of count states corresponding, respectively, to said successive voltage values so as to develop corresponding respective count outputs, said display means comprising display driving circuitry responsive to that one of said successive count outputs corresponding to said one of said successive voltage values determined by said comparator for deriving a minimum number of driving signals for displaying that one of said respective successive resistivity values corresponding to said one of said successive voltage values approximating said output signal of said electrode means.

20. The unit of claim 2, wherein said circuit means comprises a printed circuit board.

21. The unit of claim 2, wherein said electrode carrying means comprises an insulating nut having an end face which is recessed, said pair of electrodes comprising printed circuit electrodes positioned in said recessed end face of said insulating nut.

* * * * *